US012514724B2

(12) United States Patent
McDonald et al.

(10) Patent No.: US 12,514,724 B2
(45) Date of Patent: Jan. 6, 2026

(54) STENT DEVICE DELIVERY TOOL

(71) Applicant: VASCUTEK LIMITED, Renfrewshire (GB)

(72) Inventors: Gary McDonald, Strathclyde (GB); Vincent Nelis, Renfrewshire (GB)

(73) Assignee: Vascutek Limited, Renfrewshire (GB)

( * ) Notice: Subject to any disclaimer, the term of this patent is extended or adjusted under 35 U.S.C. 154(b) by 1066 days.

(21) Appl. No.: 17/311,903

(22) PCT Filed: Nov. 15, 2019

(86) PCT No.: PCT/GB2019/053238
§ 371 (c)(1),
(2) Date: Jun. 8, 2021

(87) PCT Pub. No.: WO2020/128417
PCT Pub. Date: Jun. 25, 2020

(65) Prior Publication Data

US 2022/0023081 A1 Jan. 27, 2022

(30) Foreign Application Priority Data

Dec. 20, 2018 (GB) ..................................... 1820899

(51) Int. Cl.
*A61F 2/97* (2013.01)
*A61F 2/95* (2013.01)
*A61F 2/966* (2013.01)

(52) U.S. Cl.
CPC ............... *A61F 2/97* (2013.01); *A61F 2/966* (2013.01); *A61F 2002/9511* (2013.01); *A61F 2002/9665* (2013.01)

(58) Field of Classification Search
CPC ............... A61F 2/07; A61F 2230/0095; A61F 2250/0039; A61F 2/954; A61F 2/97;
(Continued)

(56) References Cited

U.S. PATENT DOCUMENTS 4,580,568 A 4/1986 Gianturco
5,290,305 A 3/1994 Inoue
(Continued)

FOREIGN PATENT DOCUMENTS

CA 2872125 A1 4/2011
EP 0855171 A2 7/1998
(Continued)

OTHER PUBLICATIONS

Parodi, J.C., et al., "Transfemoral Intraluminal Graft Implantation for Abdominal Aortic Aneurysms," Annals of Vascular Surgery, vol. 5, pp. 491-499 (1991).

(Continued)

*Primary Examiner* — Brian A Dukert
(74) *Attorney, Agent, or Firm* — Foley Hoag LLP; Stephen J. Kenny; Nicole A. Bustos-Pomerantz

(57) ABSTRACT

The present application relates to a stent device deployment apparatus. The apparatus comprises a body having an internal bore for receiving at least a length of sheathed stent device collapsed into an un-deployed state. A bore restriction is provided for restricting passage of any stent device present in the bore to a distal end of the body. The bore restriction is configured for allowing stent device sheath material of a stent device in the bore to be accessed at the distal end of the body and pulled past the bore restriction, thereby exposing the stent device at a proximal end thereof.

14 Claims, 6 Drawing Sheets

(58) Field of Classification Search
CPC .............. A61F 2/966; A61F 2002/9511; A61F 2002/9665; A61F 2/95; A61F 2/962
See application file for complete search history.

(56) References Cited

U.S. PATENT DOCUMENTS

| | | | |
|---|---|---|---|
| 5,578,072 | A | 11/1996 | Barone et al. |
| 5,591,228 | A | 1/1997 | Edoga |
| 5,683,451 | A | 11/1997 | Lenker et al. |
| 5,824,041 | A | 10/1998 | Lenker et al. |
| 5,925,074 | A | 7/1999 | Gingras et al. |
| 6,036,723 | A | 3/2000 | Anidjar et al. |
| 6,203,568 | B1 | 3/2001 | Lombardi et al. |
| 6,635,080 | B1 | 10/2003 | Lauterjung et al. |
| 6,673,103 | B1 | 1/2004 | Golds et al. |
| 6,773,457 | B2 | 8/2004 | Ivancev et al. |
| 6,938,646 | B2 | 9/2005 | Litton |
| 7,780,622 | B2 | 8/2010 | Fitzpatrick et al. |
| 7,901,446 | B2 | 3/2011 | Fitzpatrick et al. |
| 8,088,155 | B1 | 1/2012 | Lauterjung |
| 8,088,159 | B2 | 1/2012 | Lauterjung |
| 8,092,511 | B2 | 1/2012 | Chuter |
| 8,486,129 | B2 | 7/2013 | Lautherjung |
| 8,652,195 | B2 | 2/2014 | Tani |
| 8,652,198 | B2 | 2/2014 | Andreas et al. |
| 8,740,971 | B2 | 6/2014 | Iannelli |
| 8,968,389 | B2 | 3/2015 | Greenberg et al. |
| 9,056,002 | B2 | 6/2015 | Tabor |
| 9,398,964 | B2 | 7/2016 | McGee et al. |
| 9,510,936 | B2 | 12/2016 | McDonald et al. |
| 9,622,894 | B2 | 4/2017 | McGee |
| 9,788,983 | B2 * | 10/2017 | Johnson .................... A61F 2/97 623/1.11 |
| 9,993,329 | B2 | 6/2018 | McDonald et al. |
| 10,137,021 | B2 | 11/2018 | McDonald et al. |
| 10,219,890 | B2 | 3/2019 | Madjarov et al. |
| 10,413,396 | B2 | 9/2019 | Ashton |
| 10,724,805 | B2 | 7/2020 | Barmeier et al. |
| 11,026,823 | B2 | 6/2021 | McDonald et al. |
| 11,458,008 | B2 | 10/2022 | Debus et al. |
| 11,471,261 | B2 | 10/2022 | McDonald |
| 11,554,033 | B2 | 1/2023 | Kolbel et al. |
| 12,023,236 | B2 | 7/2024 | Debus et al. |
| 2003/0024527 | A1 | 2/2003 | Ginn |
| 2003/0120263 | A1 | 6/2003 | Ouriel et al. |
| 2003/0130720 | A1 | 7/2003 | DePalma et al. |
| 2003/0135257 | A1 | 7/2003 | Taheri |
| 2003/0176911 | A1 | 9/2003 | Iancea et al. |
| 2004/0117003 | A1 | 6/2004 | Ouriel et al. |
| 2004/0167618 | A1 | 8/2004 | Shaolian et al. |
| 2004/0215315 | A1 | 10/2004 | Jones et al. |
| 2004/0243221 | A1 | 12/2004 | Fawzi et al. |
| 2005/0033399 | A1 | 2/2005 | Richter |
| 2005/0060029 | A1 | 3/2005 | Le et al. |
| 2005/0075725 | A1 | 4/2005 | Rowe |
| 2005/0137681 | A1 | 6/2005 | Shoemaker et al. |
| 2005/0230956 | A1 | 10/2005 | Igeta |
| 2006/0054537 | A1 | 3/2006 | Cholley et al. |
| 2006/0184226 | A1 * | 8/2006 | Austin ...................... A61F 2/95 623/1.11 |
| 2006/0229700 | A1 | 10/2006 | Acosta et al. |
| 2007/0010873 | A1 | 1/2007 | Neri |
| 2007/0055347 | A1 | 3/2007 | Arbefeuille |
| 2007/0106368 | A1 | 5/2007 | Vonderwalde |
| 2007/0112422 | A1 | 5/2007 | Dehdashtian |
| 2007/0135904 | A1 | 6/2007 | Eidenschink et al. |
| 2007/0168013 | A1 | 7/2007 | Douglas |
| 2007/0208409 | A1 | 9/2007 | Quigley |
| 2008/0082159 | A1 | 4/2008 | Tseng et al. |
| 2008/0147171 | A1 | 6/2008 | Ashton et al. |
| 2008/0188924 | A1 | 8/2008 | Prabhu |
| 2009/0043330 | A1 | 2/2009 | To |
| 2009/0264991 | A1 | 10/2009 | Paul, Jr. et al. |
| 2010/0152835 | A1 | 6/2010 | Orr |
| 2010/0222869 | A1 | 9/2010 | Delaney |
| 2010/0234937 | A1 | 9/2010 | Wang et al. |
| 2011/0054586 | A1 | 3/2011 | Mayberry et al. |
| 2011/0066221 | A1 | 3/2011 | White et al. |
| 2011/0190862 | A1 | 8/2011 | Bashiri et al. |
| 2011/0230956 | A1 | 9/2011 | White |
| 2012/0059448 | A1 | 3/2012 | Parker et al. |
| 2012/0136431 | A1 | 5/2012 | Chen |
| 2012/0158121 | A1 | 6/2012 | Ivancev et al. |
| 2012/0172887 | A1 | 7/2012 | Hatfield |
| 2012/0239136 | A1 | 9/2012 | Bruzzi |
| 2012/0271401 | A1 | 10/2012 | Bruszewski et al. |
| 2012/0277849 | A1 | 11/2012 | Tani et al. |
| 2012/0290068 | A1 | 11/2012 | Roeder et al. |
| 2013/0131775 | A1 | 5/2013 | Hadley et al. |
| 2013/0166015 | A1 | 6/2013 | Roeder |
| 2013/0218138 | A1 | 8/2013 | Fargahi |
| 2013/0289700 | A1 | 10/2013 | Acosta-Acevedo |
| 2013/0289713 | A1 | 10/2013 | Pearson et al. |
| 2014/0005586 | A1 | 1/2014 | Feinstein |
| 2014/0121761 | A1 | 5/2014 | McDonald et al. |
| 2014/0194970 | A1 | 7/2014 | Chobotov |
| 2014/0200648 | A1 | 7/2014 | Newell et al. |
| 2014/0249617 | A1 | 9/2014 | Argentine et al. |
| 2014/0257452 | A1 | 9/2014 | Slazas et al. |
| 2014/0277332 | A1 | 9/2014 | Slazas et al. |
| 2014/0277345 | A1 | 9/2014 | Havel et al. |
| 2014/0277359 | A1 | 9/2014 | Slazas et al. |
| 2015/0081004 | A1 | 3/2015 | Takahashi et al. |
| 2015/0105819 | A1 | 4/2015 | Becking et al. |
| 2015/0190221 | A1 | 7/2015 | Schaefer et al. |
| 2015/0257910 | A1 | 9/2015 | Duong et al. |
| 2015/0265444 | A1 | 9/2015 | Kitaoka |
| 2016/0175132 | A1 | 6/2016 | Wilger et al. |
| 2017/0014221 | A1 | 1/2017 | Kelly |
| 2018/0228593 | A1 | 8/2018 | Eaton et al. |
| 2019/0192273 | A1 | 6/2019 | Debus et al. |
| 2019/0223996 | A1 | 7/2019 | McDonald |
| 2020/0038169 | A1 | 2/2020 | Nelis |
| 2020/0038184 | A1 | 2/2020 | McLean |
| 2020/0038211 | A1 | 2/2020 | Kolbel et al. |
| 2020/0214821 | A1 | 7/2020 | McDonald |
| 2021/0204954 | A1 | 7/2021 | Nimmo |
| 2021/0212846 | A1 | 7/2021 | Shahriari |
| 2021/0228330 | A1 | 7/2021 | Kelly |
| 2021/0236257 | A1 | 8/2021 | Walzman |
| 2021/0299424 | A1 | 9/2021 | King |
| 2021/0307641 | A1 | 10/2021 | Rumbles et al. |
| 2022/0023080 | A1 | 1/2022 | Mcdonald |
| 2022/0273415 | A1 | 9/2022 | Brodie et al. |
| 2022/0378569 | A1 | 12/2022 | Mcdonald |
| 2023/0015592 | A1 | 1/2023 | Debus et al. |
| 2023/0119898 | A1 | 4/2023 | Kölbel et al. |
| 2023/0225853 | A1 | 7/2023 | Zeitani et al. |

FOREIGN PATENT DOCUMENTS

| | | | |
|---|---|---|---|
| EP | 0880979 | A1 | 12/1998 |
| EP | 1736116 | A2 | 12/2006 |
| EP | 1847236 | A2 | 10/2007 |
| EP | 2606852 | A1 | 6/2013 |
| EP | 2676639 | A1 | 12/2013 |
| EP | 3115022 | A1 | 1/2017 |
| EP | 3248572 | A1 | 11/2017 |
| EP | 3323385 | A1 | 5/2018 |
| GB | 2491477 | A | 12/2012 |
| GB | 2517689 | A | 3/2015 |
| JP | H07308330 | A | 11/1995 |
| JP | 2017042236 | A | 3/2017 |
| RU | 2720745 | C1 | 5/2020 |
| WO | WO-2004/017866 | A1 | 3/2004 |
| WO | WO-2004/064686 | A1 | 8/2004 |
| WO | WO-2006/019626 | A2 | 2/2006 |
| WO | WO-2006/034340 | A1 | 3/2006 |
| WO | WO-2006/088638 | A1 | 8/2006 |
| WO | WO-2008/057569 | A1 | 5/2008 |
| WO | WO-2008/088835 | A1 | 7/2008 |
| WO | WO-2008/112270 | A1 | 9/2008 |
| WO | WO-2009/009376 | A2 | 1/2009 |
| WO | WO-2009/082718 | A1 | 7/2009 |

(56) References Cited

FOREIGN PATENT DOCUMENTS

| | | | |
|---|---|---|---|
| WO | WO-2009/153768 | A1 | 12/2009 |
| WO | WO-2010/053563 | A1 | 5/2010 |
| WO | WO-2012/043011 | A1 | 4/2012 |
| WO | WO-2013/152327 | A1 | 10/2013 |
| WO | WO-2014/096811 | A2 | 6/2014 |
| WO | WO-2014/163957 | A1 | 10/2014 |
| WO | WO-2015/138778 | A1 | 9/2015 |
| WO | 2016054537 | A1 | 4/2016 |
| WO | WO-2016075615 | A3 | 6/2016 |
| WO | WO-2016/112378 | A1 | 7/2016 |
| WO | WO-2017/136733 | A1 | 8/2017 |
| WO | WO-2017/203056 | A1 | 11/2017 |
| WO | WO-2018/156848 | A1 | 8/2018 |
| WO | WO-2020/128418 | A2 | 6/2020 |

OTHER PUBLICATIONS

Shrestha et al., "Total aortic arch replacement with a novel 4-branched frozen elephant trunk prosthesis: Single-center results of the first 100 patients," Journal of Thoracic and Cardiovascular Surgery, 152(1): 148-159 (2016).

European Search Report issued in European Patent Application No. 17767890.1, Jul. 28, 2020, 7 pages.

International Preliminary Report on Patentability for Application No. PCT/GB2021/052337 dated Mar. 23, 2023.

International Search Report and Written Opinion of the International Searching Authority for International Application No. PCT/GB2017/052602 mailed on Jan. 9, 2018.

Levack et al., "Rapid Aortic Arch Debranching Using the Gore Hybrid Vascular Graft," Ann Thorac Surg, 95: e163-e165 (2013).

Nigro et al., "Use of the Gore Hybrid Vascular Graft in a challenging high-lying extracranial carotid artery aneurysm," J Vasc Surg, 59: 817-820 (2014).

International Search Report and Written Opinion of the International Searching Authority for International Application No. PCT/GB2019/053238 mailed on Mar. 12, 2020.

* cited by examiner

STENT DEVICE DELIVERY TOOL

CROSS SECTION TO RELATED APPLICATIONS

This application is a National Stage filing under Section 371 of International Application No. PCT/GB2019/053238, filed on Nov. 15, 2019 and published on Jun. 25, 2020 as WO 2020/128417, and claims priority to Great Britain Patent Application No. 1820899.1, filed on Dec. 20, 2018. The entire disclosures of each of the prior applications are hereby incorporated by reference herein.

FIELD OF THE INVENTION

The present invention relates to a stent device delivery tool and a method of use thereof.

BACKGROUND

In this connection, current treatment methods for aortic dissections and aneurysms predominantly utilize conventional surgical grafts and open surgery. Although endovascular treatment methods are also possible, the complexity of maintaining profusion to all major branch vessels radiating from the top of the aortic arch by purely an endovascular approach, means that endovascular treatment methods are currently very limited.

Furthermore, the use of conventional surgical grafts often necessitates a full thoracotomy, namely a major surgical opening of the chest cavity, which typically necessitates a Coronary Artery Bypass and the need to induce hypothermia and cardiac arrest. Undertaking such surgical procedures is not without risk of further complications.

Moreover, known endovascular stent device delivery systems rely on an internal delivery support shaft, typically having an integral moulded tip at its end to facilitate insertion, as well as mounting loops and release wire to support and deploy the device. This type of arrangement allows the device to be suspended from the delivery system at the tip end. It is held there until unsheathing has been performed, after which it can then be released from the delivery system. After release, which is typically by the removal of a release wire, the supporting internal central shaft and tip assembly must then be fully removed from within the stent device by retracting these items through the inside of the device lumen. These items must be removed carefully to overcome the potential risk of dislodging the previously deployed device by unintentional snagging. To provide this functionality, the delivery system typically necessitates other adjunctive elements such as a guide-wire, which would pass through the internal lumen of the shaft and tip moulding.

Such components prohibit anastomosing the non-stented end of the device to either an adjunctive device or native vessel prior to deployment of the stented section, should that be required.

An object of the present invention is to provide an improved stent delivery system that can alleviate problems associated with what is currently available.

SUMMARY OF THE INVENTION

According to the present invention there is provided stent device deployment apparatus comprising a body having an internal bore for receiving at least a length of sheathed stent device collapsed into an un-deployed state; and a bore restriction for restricting passage of any stent device present in the bore to a distal end of the body, the bore restriction being configured for allowing stent device sheath material of a stent device in the bore to be accessed at the distal end of the body and pulled past the bore restriction, thereby exposing the stent device at a proximal end thereof.

Such an apparatus simplifies the stent device delivery system in terms of its complexity, which together with the reduction in components provides the user with fewer procedural steps and potential risks, enabling a more time efficient and simplified device deployment. It moreover allows the potentially complex stent device deployment procedure to be controlled by a single user.

Furthermore, as the apparatus has no central shaft or support that projects into the vessel or lumen, a greater degree of freedom is afforded during the procedure in terms of connection options and timings. The apparatus furthermore presents the stent device as a relatively slim, stiff column with a small diameter, meaning that it can deployed in narrower vessels.

The bore may preferably comprise one or more apertures and these may take the form of two circumferential slots extending in the longitudinal direction of the bore. Alternatively, the bore restriction may take the form of one or more pins or prongs that engage with the stent device.

Conveniently, the slots subtend an angle in the range of 90 to 120 degrees circumferentially about the centre of the bore.

Conveniently, the apparatus further comprises an end collar at the distal end of the body. The inward facing walls of the body may be arranged to taper inwardly towards the end collar thereby guiding the sheathing material to the collar.

Conveniently, the body further comprises a side window allowing a section of the stent device to branch off the longitudinal axis of the sheathed section with the sheath still mounted in the body.

In this connection, the side window preferably provides a pathway, substantially perpendicular to the axis of the bore, for the stent device to pass out from the apparatus body and sheath material.

Preferably, the body comprises an openable cover for allowing access into its interior. In this way, loading and unloading of the stent device into apparatus can be facilitated.

Conveniently, the openable cover is hingeably attached.

Preferably, the cover is lockable in a closed position by way of a locking pin.

Conveniently, the locking pin is couplable to a sheath material pull strap, the pull strap further being couplable to sheath material at the distal end of the body.

Preferably, the locking pin is activated to be removed from the body to unlock the cover, only once a predetermined extent of sheath material has been pulled from the distal end of the body.

The locking pin may be coupled to the pull strap by a cord that has a controlled extent of slack relative to the extent of sheath material coupled to the pull strap.

Preferably, the apparatus further comprises a handle coupled to the body, the handle having an aperture through which the sheath material at the distal end of the body extends to the pull strap.

Conveniently, the handle is coupled to the body by way of one or more flexible members.

Conveniently, the bore has a profiled element, for example a blunt wedge element for promoting splitting of a stent device sheath within the bore.

Preferably, the wedge element presents a rounded surface to the sheath as it advances towards the distal end of the body.

According to a further aspect of the present invention there is provided a method for deploying a stent device using apparatus as claimed in any preceding claim, the method comprising the steps:—inserting an at least partially sheathed stent device within said body bore with a portion of the sheathed stent device projecting from a proximal end of the body and a distal end of the stent device abutting said restriction within the bore, wherein sheath material at the distal end of the stent device extends past said bore restriction for access at a distal end of the body; presenting the proximal end of the sheathed stent device within a target vessel; and pulling said sheath material from the distal end of the body to urge the stent device against the bore restriction, thereby allowing the sheath material to be pulled back relative to the stent device to expose the proximal end of the stent device and be deployed within the vessel.

By externalising the delivery system around the stented prosthesis, there is not the need to have a delivery shaft, mounting loops and release wire to support and deploy the device.

Furthermore, as the externalised delivery system has no central shaft or support passing through the device lumen, this enables the option of anastomosing the non-stented end of the device to either an adjunctive device (or native vessel) prior to deployment of the stented section, if that is required. In terms of connection options and timings, this increases the scope to perform the procedure.

DETAILED DESCRIPTION OF THE FIGURES

Embodiments of the present invention will now be describe by way of example and with reference to the following drawings, of which:—

DETAILED DESCRIPTION FOR CARRYING OUT THE INVENTION

Figure 1:
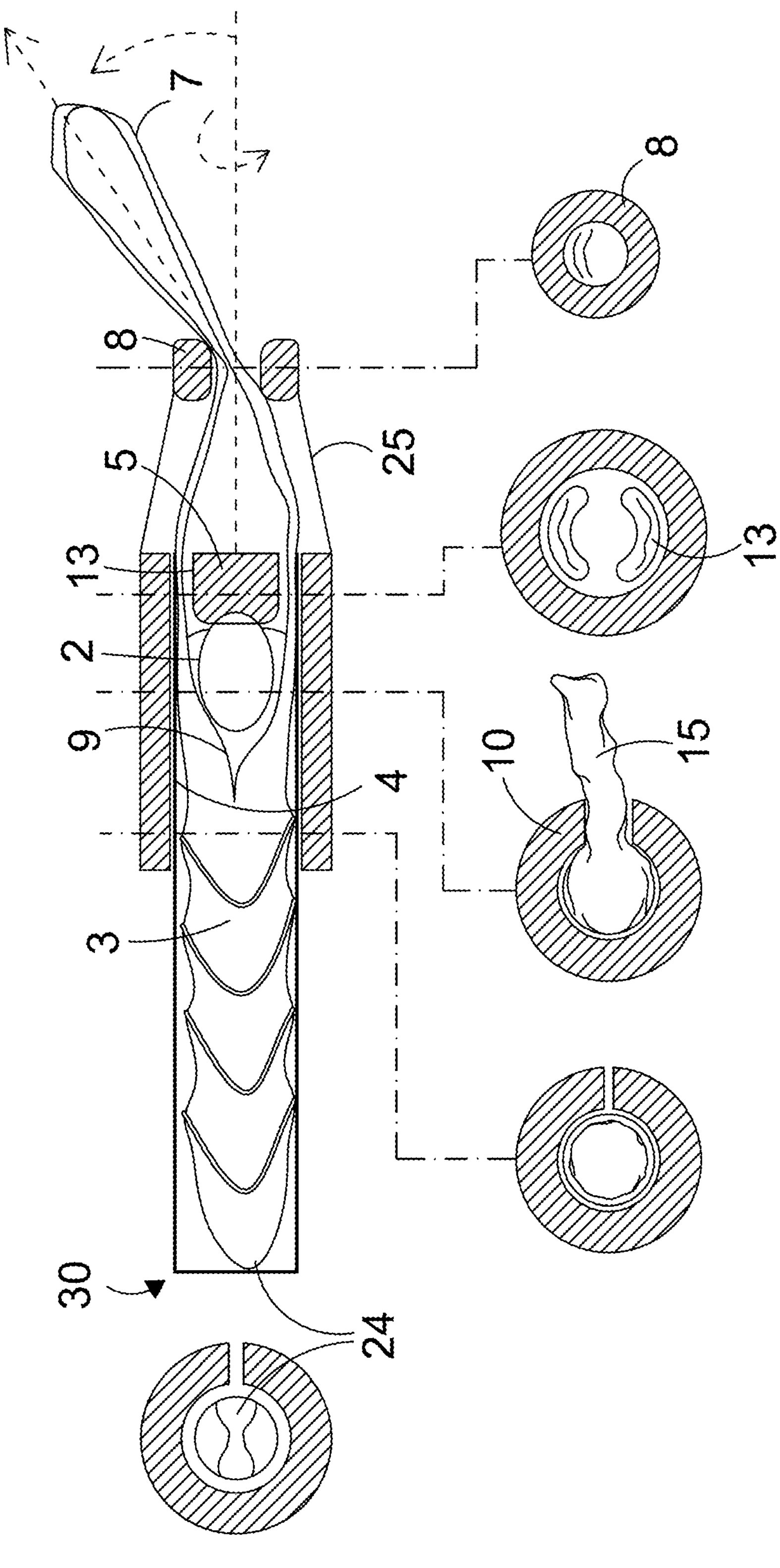
FIG. 1 shows a cross-sectional view of the apparatus of the present invention with a compatible stent device in place, in accordance with an aspect of the present disclosure.

FIG. 1 shows a cross-sectional view of the apparatus 1, having a body 2 into which a compatible sheathed stent device 3 is located.

In this regard, the body has a bore 4, dimensioned to allow the sheathed stent device 3 to sit within the bore, but not so tight so as to prevent the sheath material from moving relative to the bore and the stent device.

Figure 7A:
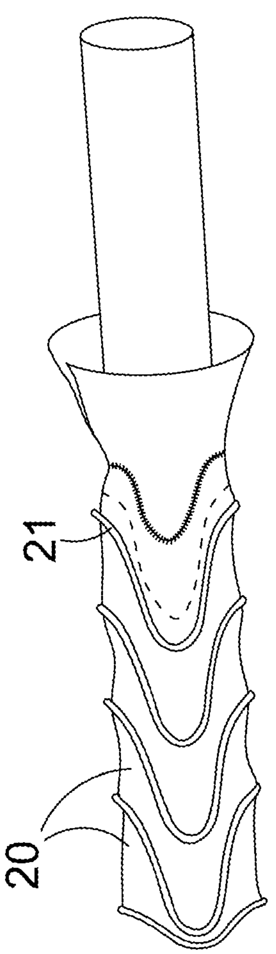
FIGS. 7A and 7B show views of a compatible stent device for use with the present invention, in accordance with an aspect of the present disclosure.
Figure 7B:
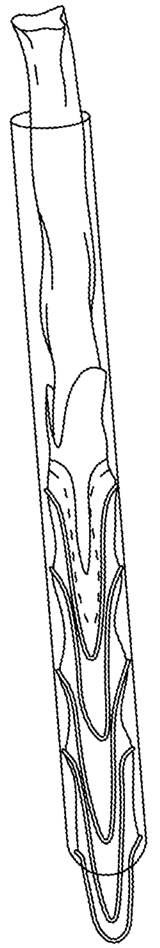
Figure 8:
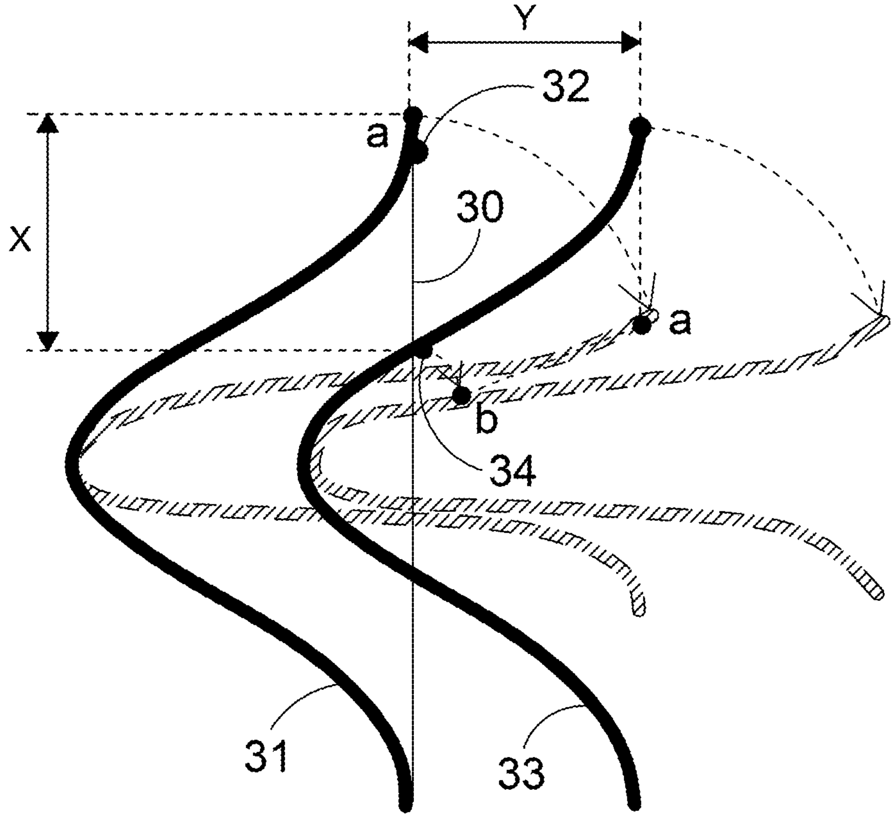
FIG. 8 is a schematic view showing adjacent ring elements of a compatible stent device for use with the present invention, in accordance with an aspect of the present disclosure.

The compatible sheathed stent device 3 for use with the apparatus is shown in FIGS. 7A and 7B. This preferably comprises a lumen or sleeve of fabric, typically gel coated polyester, fitted with a series of spring like “stent elements” 20, typically having ring elements 21 formed from nitinol wire in the shape of an undulating Z or in the preferred embodiment a saddle ring, namely a hyperbolic paraboloid.

Multiple ring elements 21 of the compatible sheathed stent device are located along the axis of the lumen and these are attached circumferentially to the fabric by sutured thread, to form the stented device section, which has the capacity to be constrained into a significantly smaller diameter tube, namely the sheath.

When compacted into a small calibre sheath as shown in FIG. 7B, the compatible sheathed stent device (with an appropriate selected oversize) can be readily inserted into the lumen of a branch vessel. Removing the sheath from the stent device enables it to be deployed into the native vessel, where the stented section expands radially outwards. The radial expanding stent elements contact and push onto the internal vessel wall to create a snug fitting non-sutured sealed junction.

The overlapping nature of the ring elements in the compacted configuration affords the sleeve with a column stiffness facilitating use with deployment apparatus.

In this example of the compatible device, the sheath may be configured with a relative high saddle height and a ring inter spacing which is less than the saddle height, to provide an overlap of the peaks and valleys of adjacent rings. This property in combination with an adjacent section of supported fabric is utilised to maintain the position of the stent device relative to the body 2, prior to and during the unsheathing process.

As shown in FIG. 1, at or near the distal end of the stented section of the compatible device, there may be provided a section of flexible crimped fabric 15, typically gel coated polyester, which is joined and attached by suturing to form a blood tight continuous endoprothesis lumen. In some embodiments this section may also include a “Y” branch lumen. The non-stented section is provided to enable an endoprothesis to be joined by suturing to either the main prosthesis body or alternatively to a healthy section of native vessel, to reinstate blood profusion to the native branch vessel.

The sheath of the compatible stent device is preferably thin walled (typically a PTFE material), which has an inherent preposition to tear linearly, without the need for additional grooves or perforations. The sheath may have three sections: a proximal circular section, which has a length slightly longer than the length of the compacted stented section, a tail section at its distal end and a mid-section, where the circular section splits and propagates into the two tail elements.

These flat ribbon like tail elements 7 originate from the end of the circular section and can be formed by folding. The formed tails are fed through or past a restriction 5 within the body 2 and out into a separate strap element, where they can be tied together to form a singular user interface for sheath removal.

As shown in FIG. 1, the restriction 5 in the bore 4 is configured to obstruct travel of the stent device. The restriction however allows stent device sheath material, namely the tails 7 to pass the restriction for access at the distal end of the body 2. The sheath material exits the body by way of a collar 8, whose core aperture has rounded exit surfaces to allow the sheath material to be pulled from a wide range of angles on exiting the body 2.

Whilst any suitable means may be employed to allow passage of the sheath material past the restriction, in the embodiment shown in FIG. 1 two arcuate apertures 13 are provided in the face of the restriction 5, the apertures extending longitudinally in the axial direction of the body.

The apertures are substantially circumferential and subtend an angle of 90 to 120 degrees. In this connection, the apertures each provide passage for a tail of sheath material 7, the sheath material being split within the bore 4 at point 9.

The body has a side window 10 for allowing the sheathed stent device to be positioned within the body with a crimped section 15 of the stent device exiting the body to the side via the window. The side window hence provides a pathway for the non-stented device fabric to pass through out from the confines of body 2 substantially perpendicularly to the axis of the sheathed sheath, enabling access to the distal end of the stent device. This end can hence be trimmed in length to suit individual patient anatomy and facilitates suturing to an adjunctive graft or native vessel.

A sequence of use of embodiments of the apparatus of the present invention is shown in FIGS. 2A to 6D.

Figure 2A:
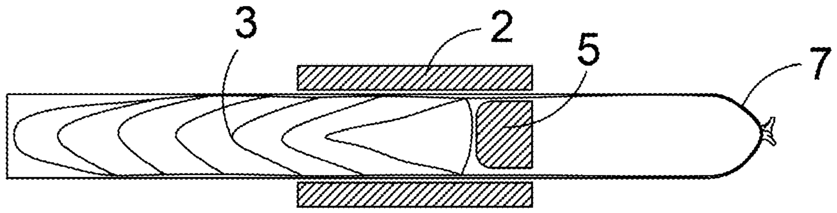
FIGS. 2A to 6D show the stages of operation of embodiments of the present invention in deploying a compatible stent device, in accordance with an aspect of the present disclosure.
Figure 2B:
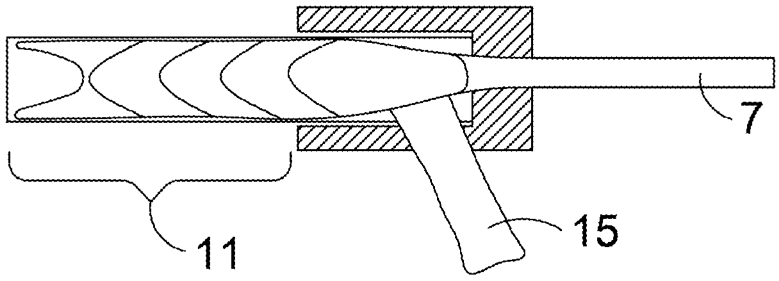

As shown in FIGS. 2A and 2B, the compatible sheathed stent device 3 is inserted into the body of the apparatus with tails 7 of the sheath projecting from the distal end, and a sheathed stent device section 11 projecting from the proximal end of the body. The sheathed section 11 is relatively rigid, by virtue of the interaction of the compressed stent device material, wishing to expand against the inside surface of the sheathing material. As such it can be readily and accurately manipulated and moved into position within a vessel or lumen requiring the stent procedure.

In this regard, the compatible stent device is preferably formed of imbricated ring elements, which are configured and arranged on a fabric lumen, so when compacted and constrained within the sheath material 7, they contribute to provide an element, which exhibits a high degree of column stiffness.

Figure 3:
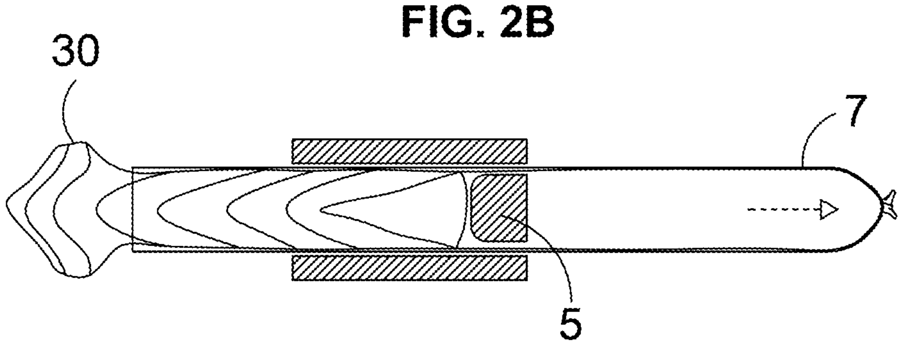
Figure 4:
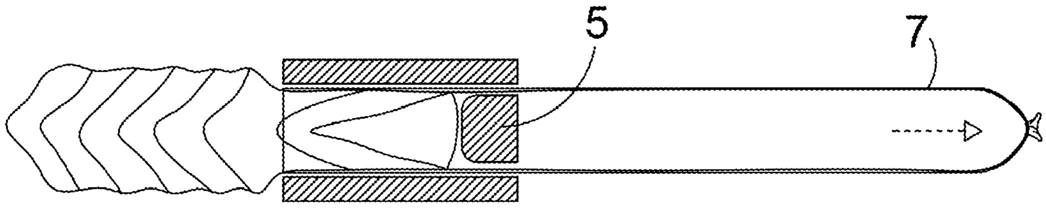
Figures 5A, 5B, 5C:
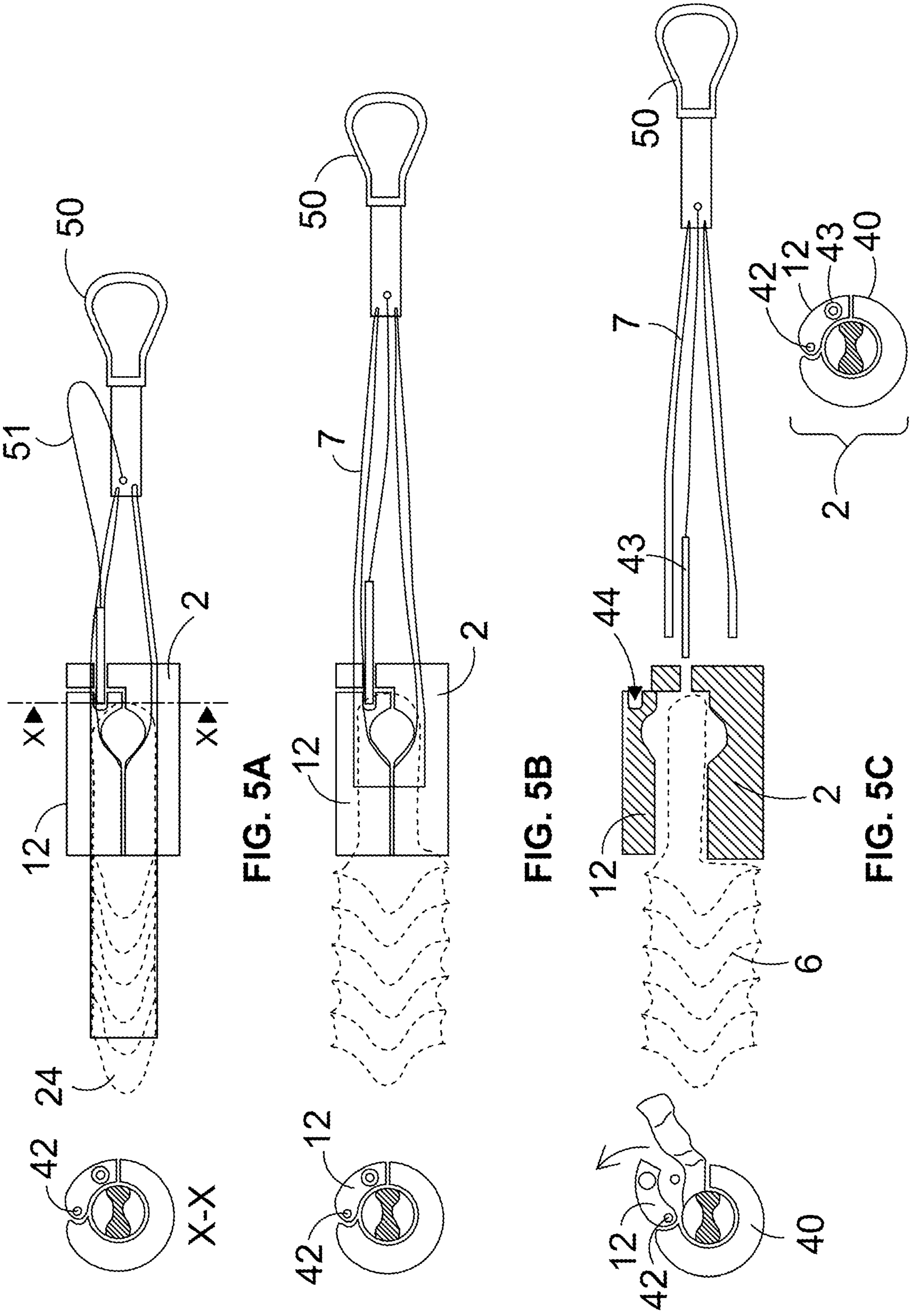

Once in position within the lumen or vessel, pulling the sheath material tails 7 draws the stent device into engagement with the restriction 5 so that the stent device itself cannot move further. In so doing, further pulling of the sheathing material results in the sheathing material being pulled back from the proximal end 30 of the stent device so that the stent device becomes exposed at its proximal end and hence can expand towards the deployed state within the lumen or vessel. This is illustrated in FIG. 3. FIG. 4 shows the tails 7 being pulled yet further to expose more of the stent device so that more of it can deploy within the lumen or vessel.

As shown in FIG. 1, the distal end 25 of the body 2 is tapered to guide the sheathing material towards the collar 8. In this connection, exit surfaces of the collar 8 are rounded to allow the tails to be pulled over a wide range of angles without tearing or fracturing.

Once the stent device has been sufficiently deployed, it can be removed from the body 2 of the apparatus.

In this respect, FIGS. 5A to 5C and FIGS. 6A to 6D show an embodiment having a hinged cover 12, whereby the body can be opened to release the stent device, post unsheathing and once deployed. With this embodiment, deployment of the stent device by a single user is further facilitated.

In this connection, the body 2 takes the form of an opening clasp body 2 configured to hold, encase and support the stent device for insertion and unsheathing, which also facilitates removal from the device post unsheathing and deployment by the utilisation of a hinged cover element 12, namely a clasp lid which forms part of the body 2.

The body 2 provides a near circular encasement around the sheath split region and comprises a clasp housing 40, clasp lid 12, pivot 42 and locking pin 43.

The clasp body 2 is held closed through the locking pin 43 which is engaged within a pocket cavity 44 of the clasp lid. The engaged position is maintained throughout the deployment process up until the sheath has been fully removed from the stented section of the device.

The other end of the locking pin 43 is attached to the pull strap 50 through a link element 51, which in one embodiment may be a flexible resilient cord 51 of a specified length, which enables the pull strap to be engaged and pulled by the user to facilitate device deployment. The cord length is specifically configured to provide a controlled amount of slack to ensure that the pin is not in tension. The locking pin 43 remains engaged up until the sheath has been fully removed from the stented device section. In this respect the sheath material 7 is also coupled to the pull strap, so that the action of pulling the pull strap first applies tension to the sheath material at the distal end of the apparatus.

When the applied pull has taken up the pre-slack within the cord, this pull action is then transmitted to the locking pin, causing it to slide out from its engagement within the clasp lid pocket 44.

In another embodiment, the flexible cord element may be replaced with a resilient wire, which has an integral stop feature, that permits a pre-determined amount of sliding prior to engagement of the said stop feature.

Once the locking pin 43 is removed from the clasp lid 12, the lid is then free to pivot open to facilitate removal of the clasp body 2 from the deployed stent device 6.

Beneficially, the clasp body 2 fully supports the compacted compatible stent device 3 throughout the deployment process and that the lid 12 is only allowed to open towards the end of the sheath removal process, which can be performed in one continuous seamless movement without the need for a user to act on another deployment step.

Figure 6D:
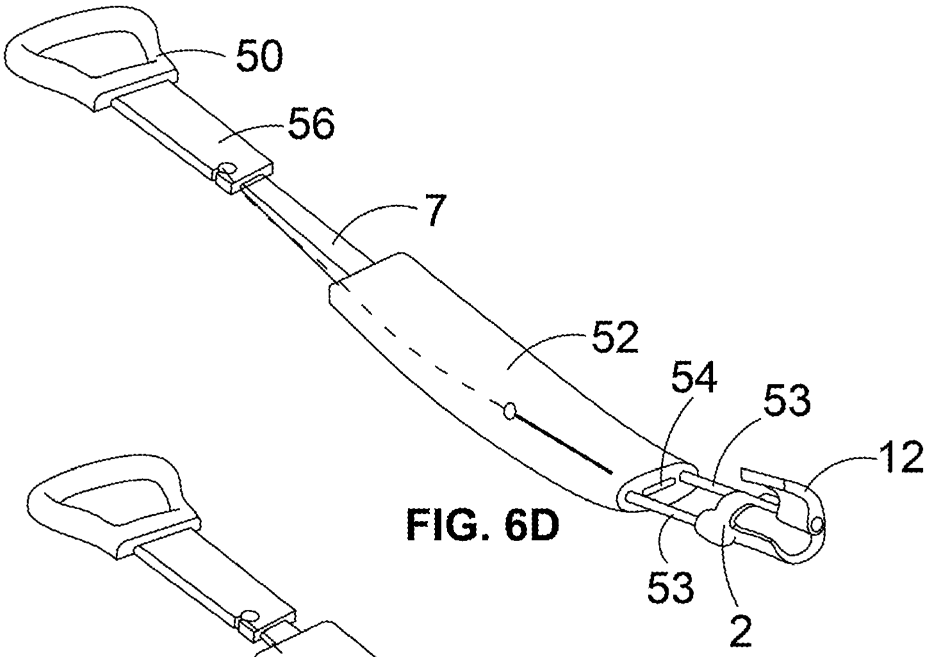
Figure 6C:
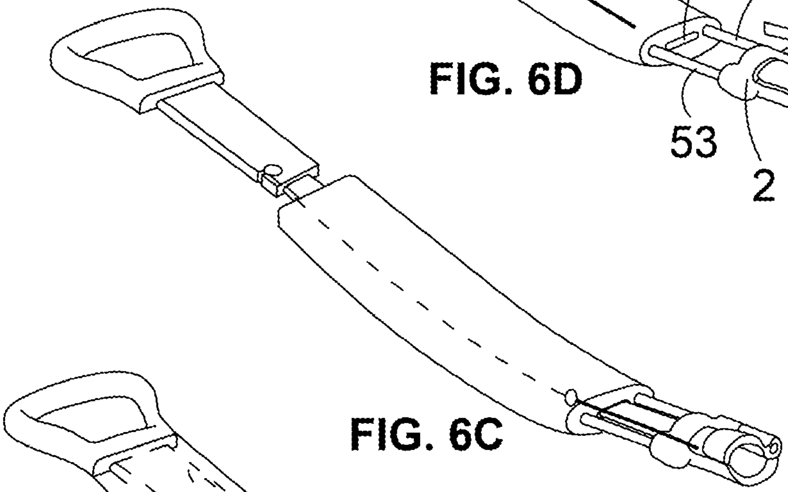
Figure 6B:
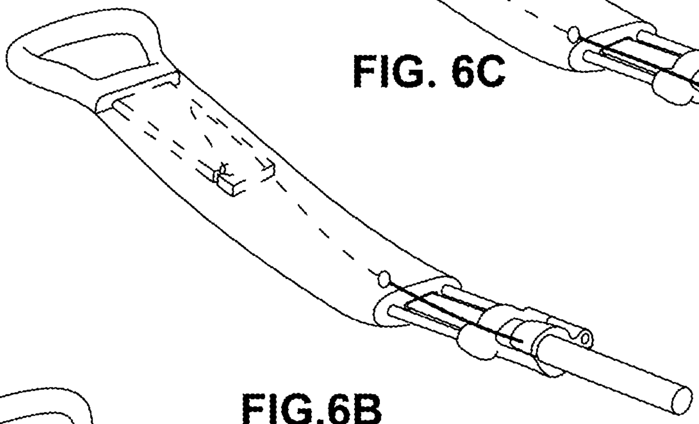
Figure 6A:
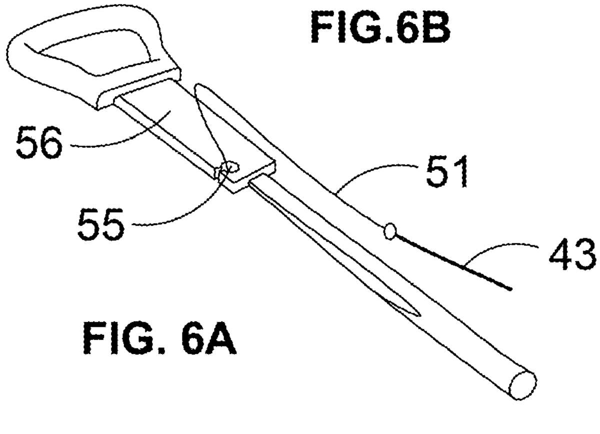

As shown in FIGS. 6A to 6D, the pull strap 50 includes a handle 52 connected to the clasp body 2 by one or more connectors 53. The connectors 53 are preferably formed of flexible material allowing the handle to be maneuvered so as to be angled with respect to the body, as shown in FIG. 6B. This allows a user to manipulate the deployment apparatus in order to have better access for stent device deployment.

The handle 52 includes a through channel 54 through which the sheath material 7, locking pin 43 and cord 51 can pass as shown in FIG. 6B. The cord from the pin 43 passes up the channel 54 and attaches to an aperture 55 in a key blade element 56 of the pull strap handle 50. The key blade element slots neatly away into the handle aperture prior to deployment of the stent device and withdrawal of the locking pin 43 from the cavity 44.

With the above apparatus, the body 2 holds and supports the compatible sheathed stent device 3 to enable the proximal compacted section to be inserted into either a native vessel or an adjunctive stent device body, so that it can be held for subsequent unsheathing and deployment to then enable vessel profusion to be reinstated.

This simplifies the delivery system in terms of its complexity, which together with the reduction in components provides the user with fewer procedural steps and potential risks, enabling a more time efficient and simplified device deployment.

The internal arrangement within the body enables controlled parting of the sheath when the user pulls the strap element. When the sheath is pulled across the internal bore restriction, the circular lumen aspect of the sheath is caused to continue to split, propagating along the two tail elements 7. Simultaneously, the movement applied at the strap is transmitted to the proximal end of the sheath, causing it to slide over the stent device, enabling the compacted stent device to be relieved from its radial constraint. In doing so, the stent device opens and engages the internal lumen of the vessel.

As shown in FIGS. 1 and 5, the compatible stent may have an integral stent device tip 24 feature. As shown in FIG. 5, this may be provided at the proximal end of the stented region of the stent device, which when compacted within the sheath constraint also protrudes beyond the end of the sheath to partially expose said compacted stent device elements covered in soft suture (or PTFE thread) to provide an atraumatic tip like feature.

Whilst the restriction 5 is shown as an abutment within the bore 4, it may take the alternative suitable forms, such for example as pins or prong elements that temporarily inter-engage with formations such as eyelets or pockets attached to or formed on the stent device, to provide an alternative arrangement to hold and locate the compatible stent device within the body during unsheathing and deployment steps.

The body 2 may further have guide channels for the sheath to be drawn apart in a direction substantially perpendicular to the axis of the sheath, in so doing facilitating efficient low force splitting and removal of the sheath from the compacted device, while also providing a cavity location feature for accommodating additional device features (re-cuff element) adjacent to the stented section. This may also provide sufficient encasement of this fabric, or retention of it, to enable it to be utilized as a fabric backstop.

The collar 8 at the end of the body may further incorporate one or more rollers to facilitate the tails being pulled over a range of angles relative to the sheath axis. As may be recognized by those of ordinary skill in the art based on the teachings herein, numerous changes and modifications may be made to the above-described and other embodiments of the present disclosure without departing from the scope of the disclosure. The components of the implants as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component (s) or feature(s) to provide a similar function for the intended purpose. In addition, the implants may include more or fewer components or features than the embodiments as described and illustrated herein. Accordingly, this detailed description of the currently-preferred embodiments is to be taken in an illustrative, as opposed to limiting of the disclosure.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The disclosure has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the disclosure be construed as including all such modifications and alterations.

The invention claimed is:

1. A stent device deployment apparatus comprising:

a body having an internal bore for receiving at least a length of sheathed stent device collapsed into an undeployed state; and a bore restriction for restricting passage in a distal direction of any stent device present in the bore to a distal end of the body, the bore restriction being configured for allowing stent device sheath material of a stent device in the bore accessed at the distal end of the body and pulled past the bore restriction, thereby exposing the stent device at a proximal end thereof; and wherein the body comprises an openable cover for allowing access into its interior and optionally, wherein the openable cover is hingeably attached;

wherein the cover is lockable in a closed position by way of a locking pin couplable to a sheath material pull strap, the pull strap couplable to a sheath material at the distal end of the body, and the locking pin is activated to be removed from the body to unlock the cover, only once a predetermined extent of the sheath material has been pulled from the distal end of the body;

wherein the locking pin is coupled to the pull strap by a cord that has a controlled extent of slack relative to the extent of the sheath material coupled to the pull strap; and a handle coupled to the body, the handle having an aperture through which the sheath material at the distal end of the body extends to the pull strap and optionally, wherein the handle is coupled to the body by way of one or more flexible members.

2. An apparatus according to claim 1, wherein the bore restriction has one or more apertures.

3. An apparatus according to claim 2, wherein the one or more apertures comprise two circumferential slots extending through the restriction in the longitudinal direction of the bore.

4. An apparatus according to claim 3, wherein the slots each subtend an angle in the range of 90 to 120 degrees circumferentially about the centre of the bore.

5. An apparatus according to claim 1, further comprising an end collar at the distal end of the body.

6. An apparatus according to claim 5, wherein inward facing walls of the body taper inwardly towards the end collar.

7. An apparatus according to claim 1, wherein the body further comprises a side window; and optionally, wherein the side window provides a pathway, substantially perpendicular to an axis of the bore, for the stent device to pass out from the apparatus body and sheath material.

8. An apparatus according to claim 1, wherein the bore has a profiled element for promoting splitting of a stent device sheath within the bore.

9. An apparatus according to claim 8, wherein the profiled element is a wedge member.

10. An apparatus according to claim 1, wherein the body comprises a substantially circular tube with a longitudinal slot.

11. An apparatus according to claim 1, for use with a stent device which is deployable from a compressed substantially rigid configuration to a radially expanded configuration.

12. An apparatus according to claim 11, wherein the stent device is formed of imbricated ring elements.

13. An apparatus according to claim 1, further comprising a length of sheathed stent device collapsed into an un-deployed state and, loaded into the body ready for deployment.

14. A method for deploying a stent device using the apparatus as claimed in any preceding claim, the method comprising the steps:

inserting an at least partially sheathed stent device within said body bore with a portion of the sheathed stent device projecting from a proximal end of the body and a distal end of the stent device abutting said restriction within the bore, wherein sheath material at the distal end of the stent device extends past said bore restriction for access at a distal end of the body;

presenting the proximal end of the sheathed stent device within a target vessel; and pulling the-sheath material from the distal end of the body to urge the stent device against the bore restriction, thereby allowing the sheath material to be pulled back relative to the stent device to expose the proximal end of the stent device and be deployed within the vessel.

* * * * *